United States Patent
Pan et al.

(10) Patent No.: US 12,392,698 B2
(45) Date of Patent: Aug. 19, 2025

(54) SYSTEM AND METHOD FOR TESTING ROCK FRACTURE UNDER VACUUM AND EXTREME-TEMPERATURE CONDITION

(71) Applicant: Institute of Rock and Soil Mechanics, Chinese Academy of Sciences, Wuhan (CN)

(72) Inventors: Pengzhi Pan, Wuhan (CN); Yujie Feng, Wuhan (CN); Zhaofeng Wang, Wuhan (CN)

(73) Assignee: Institute of Rock and Soil Mechanics, Chinese Academy of Sciences, Wuhan (CN)

( * ) Notice: Subject to any disclaimer, the term of this patent is extended or adjusted under 35 U.S.C. 154(b) by 0 days.

(21) Appl. No.: 19/066,280

(22) Filed: Feb. 28, 2025

(65) Prior Publication Data
US 2025/0198894 A1    Jun. 19, 2025

(30) Foreign Application Priority Data
Aug. 30, 2024 (CN) .......................... 202411209243.6

(51) Int. Cl.
*G01N 3/10* (2006.01)
*G01N 3/24* (2006.01)
(Continued)

(52) U.S. Cl.
CPC ................ *G01N 3/10* (2013.01); *G01N 3/24* (2013.01); *G01N 29/14* (2013.01); *G01N 2203/0019* (2013.01); *G01N 2203/0048* (2013.01); *G01N 2203/0067* (2013.01); *G01N 2203/0222* (2013.01); *G01N 2203/0226* (2013.01); *G01N 2203/0228* (2013.01); *G01N 2203/0234* (2013.01); *G01N 2203/0252* (2013.01)

(58) Field of Classification Search
CPC ........... G01N 3/10; G01N 3/18; G01N 33/24; G01N 29/14; G01N 2203/0067; G01N 2203/0226; G01N 2203/0228; G01N 2203/0234; G01N 2203/0019; G01N 2203/0048; G01N 2203/0222; G01N 2203/0252
See application file for complete search history.

(56) References Cited

FOREIGN PATENT DOCUMENTS

| CN | 107831086 A | 3/2018 |
|----|-------------|--------|
| CN | 107907413 A | 4/2018 |

(Continued)

*Primary Examiner* — Jonathan M Dunlap

(57) ABSTRACT

A system for testing rock fracture under a vacuum and extreme-temperature condition includes a vacuum extreme-temperature loading structure, an overall loading frame structure and a mobile cart. The vacuum extreme-temperature loading structure includes a vacuum transparent shield, a vacuum base and an extreme-temperature loading module. A bottom end of the vacuum transparent shield is covered on the vacuum base and is hermetically connected with the vacuum base to form a vacuum structure. The extreme-temperature loading module is provided inside the vacuum structure. The overall loading frame structure includes an overall frame and a loading cylinder. A middle of the overall frame is provided with a loading space, and the vacuum extreme-temperature loading structure is located in the loading space. The mobile cart is located in the loading space and is slidably connected with the overall frame, and the vacuum base is arranged on the mobile cart.

8 Claims, 6 Drawing Sheets

(51) Int. Cl.
*G01N 33/24* (2006.01)
*G01N 29/14* (2006.01)

(56) References Cited

FOREIGN PATENT DOCUMENTS

| | | |
|---|---|---|
| CN | 112683677 A | 4/2021 |
| CN | 215677861 U | 1/2022 |
| CN | 115096936 A | 9/2022 |
| CN | 115389331 A | 11/2022 |
| CN | 116256245 A | 6/2023 |
| WO | 2021047145 A1 | 3/2021 |

SYSTEM AND METHOD FOR TESTING ROCK FRACTURE UNDER VACUUM AND EXTREME-TEMPERATURE CONDITION

CROSS-REFERENCE TO RELATED APPLICATIONS

This application claims the benefit of priority from Chinese Patent Application No. 202411209243.6, filed on Aug. 30, 2024. The content of the aforementioned application, including any intervening amendments thereto, is incorporated herein by reference in its entirety.

TECHNICAL FIELD

This application relates to rock mechanics laboratory testing technology, and more specifically to a system and method for testing rock fracture under a vacuum and extreme-temperature condition.

BACKGROUND

With the increasing depletion of resources on the Earth and continuous advancements in deep space exploration technology, nations worldwide have launched a series of deep space exploration programs targeting celestial bodies such as the Moon, Mars, and asteroids. These programs encompass extraterrestrial celestial body sampling, in-situ utilization of extraterrestrial regolith resources, and construction of extraterrestrial base stations. The lunar surface experiences extreme temperature fluctuations ranging from −233° C. to 123° C., while Mars exhibits a temperature range of −143° C. to 35° C. The Moon has an extremely low atmospheric pressure of approximately $3 \times 10^{-13}$ kPa, whereas Mars has a slightly higher atmospheric pressure of about 0.7 kPa. Under such extreme conditions, the rocks and soils on the Moon and Mars demonstrate physical and mechanical properties fundamentally distinct from terrestrial geotechnical materials. A comprehensive understanding of the physical-mechanical behavior of these extraterrestrial regolith materials under extreme environments is crucial to ensure the success of deep space exploration missions.

Currently, low-temperature environments are predominantly created by compressor refrigeration and liquid nitrogen refrigeration. Unfortunately, the compressor refrigeration is limited by power and size, making it unsuitable for large-scale rock mechanics testing, and struggles to achieve ultralow temperatures below −150° C. The liquid nitrogen refrigeration typically involves immersing specimens in liquid nitrogen, which subjects the samples to thermal shock that may compromise experimental results. Furthermore, direct liquid nitrogen immersion cannot be combined with vacuum environments, and the immersion process presents operational complexity and safety risks. In addition, most existing loading devices are incapable of conducting alternating ultralow-temperature and high-temperature testing. Rock deformation measurements are instable under high-temperature conditions, while observation methods for rock fracture under ultralow temperatures are constrained by interference factors such as frost formation, fogging, and airflow disturbances in low-temperature environments.

Therefore, how to provide a rock fracture testing system capable of integrating vacuum environments with extreme high/low temperature conditions, while enabling quantitative investigation of rock fracture characteristics under vacuum and extreme-temperature environments is a critical technical issue required to be solved by those skilled in the art.

SUMMARY

To address the problems existing in the prior art, an objective of the present invention is to provide a system for testing rock fracture under a vacuum and extreme-temperature condition, which can realize rock loading under the coupling of vacuum environment and extreme high/low temperature environment, synchronously monitor the deformation evolution of the rock rupture, and obtain the surface deformation field and acoustic emission response characteristics.

Technical solutions of the present disclosure are described below.

In a first aspect, this application provides a system for testing rock fracture under a vacuum and extreme-temperature condition, comprising:
  a vacuum extreme-temperature loading structure;
  an overall loading frame structure; and
  a mobile cart;
  wherein the vacuum extreme-temperature loading structure comprises a vacuum transparent shield, a vacuum base, and an extreme-temperature loading module; a bottom end of the vacuum transparent shield is covered on the vacuum base and is hermetically connected with the vacuum base to form a vacuum structure; and the extreme-temperature loading module is provided inside the vacuum structure;
  the overall loading frame structure comprises an overall frame and a loading cylinder; a middle of the overall frame is provided with a loading space, and the vacuum extreme-temperature loading structure is located in the loading space; a center of a top end of the overall frame is provided with a first loading through hole, and the loading cylinder is located above the first loading through hole to enable a loading rod of the loading cylinder to pass through the first loading through hole to apply a loading force to the extreme-temperature loading module; an end of the loading cylinder is fixedly connected with the overall frame; and
  the mobile cart is located in the loading space and is slidably connected with the overall frame, and the vacuum base is arranged on the mobile cart.

In some embodiments, the overall frame comprises a frame bottom column, a frame column and a frame crossbeam;
  a sliding guide rail is provided on the frame bottom column, and pulleys of the mobile cart are adapted to the sliding guide rail; and the mobile cart is slidably connected to the frame bottom column;
  the frame column is provided with a loading space; and the frame column is located above the frame bottom column and is fixedly connected to the frame bottom column;
  the frame crossbeam is located above the frame column and is fixedly connected to the frame column; and
  a center of the frame crossbeam is provided with a first loading through hole; and the loading cylinder is located above the first loading through hole and is fixedly connected to the frame crossbeam.

In some embodiments, the overall loading frame structure further comprises two counterweight structures, two counterweight support frames and two counterweight ropes;

each of the two counterweight support frames is in a right-angled triangular structure; the two counterweight support frames are symmetrically along an axis of the loading cylinder and are fixedly arranged at a first end of the loading cylinder; a leg of one of the two counterweight support frames is parallel to a leg of the other of the two counterweight support frames; two ends of a hypotenuse of each of the two counterweight support frames are each fixedly provided with a support pulley; and one end of each of the two counterweight ropes is fixedly connected to a counterweight structure corresponding thereto through a first counterweight hook, and the other end of each of the two counterweight ropes successively passes through the support pulley corresponding thereto and is fixedly connected to the top of the vacuum transparent shield through a second counterweight hook.

In some embodiments, the overall loading frame structure further comprises a displacement sensor, and the displacement sensor is located at a center of a second end of the loading cylinder.

In some embodiments, the vacuum extreme-temperature loading structure further comprises a vacuum pumping pipe; and a first end of the vacuum pumping pipe is located inside the vacuum transparent shield;

the vacuum base is provided with a vacuum pipe through hole; a second end of the vacuum pumping pipe passes through the vacuum pipe through hole to be connected to a vacuum pump; and an observation port is provided on one side of the vacuum transparent shield, and is sealed with a transparent anti-fog material.

In some embodiments, the extreme-temperature loading module comprises:
a vacuum support frame;
a first loading bracket;
a second loading bracket;
two longitudinal deformation sensors;
a first loading pad;
a second loading pad;
a first thermal isolation plate;
a second thermal isolation plate;
a loading block; and
a pressure head;
wherein the vacuum support frame is located at the center of the vacuum base;
the first loading bracket and the second loading bracket are each circular, and central axes of the first loading bracket and the second loading bracket are the same as a central axis of the vacuum base; the second loading bracket is located on and fixedly connected to the vacuum support frame; and each of the first loading bracket and the second loading bracket is provided with two symmetrical longitudinal support holes;
one end of each of the two longitudinal deformation sensors is configured to pass through a longitudinal support hole corresponding thereto to be fixedly connected to the first loading bracket, and the other end of each of the two longitudinal deformation sensors is configured to pass through a longitudinal support hole corresponding thereto to be fixedly connected to the second loading bracket;
the first loading pad and the second loading pad are each cylindrical, and central axes of the first loading pad and the second loading pad are the same as the central axis of the vacuum base; the second loading pad is located above and fixedly connected to the second loading bracket, and the first loading pad is located below and fixedly connected to the first loading bracket;
the first thermal insulation plate and the second thermal insulation plate are each circular, and central axes of the first thermal insulation plate and the second thermal insulation plate are the same as the central axis of the vacuum base; the first thermal insulation plate is located above and fixedly connected to the first loading pad, and the second thermal insulation plate is located above and fixedly connected to the second loading bracket;
the loading block is located at a center of the first thermal insulation plate and is fixedly connected to the first thermal insulation plate;
the pressure head is cylindrical, and a position of the pressure head corresponds to that of the loading block; and
a top end of the vacuum transparent shield is provided with a second loading through hole; and one end of the pressure head passes through the second loading through hole and is hermetically and slidably connected to the vacuum transparent shield.

In some embodiments, the extreme-temperature loading module further comprises:
a heat conduction cavity;
two sample pads;
a first vacuum liquid nitrogen delivery circulating pipe;
a second vacuum liquid nitrogen delivery circulating pipe;
a liquid nitrogen refrigeration circulating pipe; and
a plurality of electromagnetic heating plate;
wherein the heat conduction cavity has a cubic hollow structure and is located on the second thermal insulation plate; a center of one side of the heat conduction cavity is provided with an observation channel adapted to a rock sample, and a position of the observation channel corresponds to that of the observation port; a top of the heat conduction cavity is provided with two through holes for liquid nitrogen circulating pipes, and is also provided with a third loading through hole;
the two sample pads are located inside the heat conduction cavity, and central axes of the two sample pads are the same as the central axis of the vacuum base; a uniaxially compressed rock sample is arranged between the two sample pads; one of the two sample pads is located at a bottom of the heat conduction cavity, and the other of the two sample pads is configured to pass through the third loading through hole to abut against the first loading pad;
a first end of the first vacuum liquid nitrogen delivery circulating pipe is connected to an outlet of a liquid nitrogen circulation tank, and a first end of the second vacuum liquid nitrogen delivery circulating pipe is connected to an inlet of the liquid nitrogen circulation tank;
a first end of the liquid nitrogen refrigeration circulating pipe is connected to the second end of the first vacuum liquid nitrogen delivery circulating pipe;
the plurality of electromagnetic heating plates are arranged in the heat conduction cavity and closely against an inner side wall of the heat conduction cavity; and
the vacuum base is also provided with two vacuum liquid nitrogen delivery holes and an electromagnetic heating guide hole; a second end of the liquid nitrogen refrigeration circulating pipe is configured to passes through one of the two vacuum liquid nitrogen delivery holes and one of the two liquid nitrogen circulating pipe through holes in sequence to enter the heat conduction cavity; the second end of the liquid nitrogen refrigeration circulating pipe is arranged at intervals with the plurality of the electromagnetic heating plates closely against the inner side wall of the heat conduction cavity, and then passes through the other of the two liquid nitrogen circulating pipe through holes and the other of the two vacuum liquid nitrogen delivery holes in sequence to be connected to the second end of the second vacuum liquid nitrogen delivery circulating pipe; and the plurality of electromagnetic heating plates are connected in series through electromagnetic heating wires and pass through the electromagnetic heating guide hole to be connected to a power supply.

In some embodiments, the extreme-temperature loading module further comprises a transverse deformation sensor, a temperature sensor and an acoustic emission sensor;

two ends of the transverse deformation sensor are configured to abut against and be fixed to the outer side wall of the heat conduction cavity;

the temperature sensor is arranged inside the heat conduction cavity; and the acoustic emission sensor is arranged inside the heat conduction cavity.

In some embodiments, the extreme-temperature loading module further comprises a dual-channel proportion integration differentiation (PID) controller and a vacuum liquid nitrogen delivery circulating pipe;

the vacuum liquid nitrogen delivery circulating pipe comprises a pressure sensor and an electric heater; both the pressure sensor and the electric heater are arranged at an inlet of the vacuum liquid nitrogen conveying circulating pipe, and the pressure sensor and the electric heater are respectively connected to the first channel of the dual-channel PID controller; and the plurality of electromagnetic heating plates are connected in series through an electromagnetic heating wire, and pass through the electromagnetic heating guide hole to be connected to the second channel of the dual-channel PID controller; and the dual-channel PID controller is connected to the power supply.

In a second aspect, this application provides a method for testing rock fracture under a vacuum and extreme-temperature condition using the above system, comprising:

preparing speckles for a uniaxially compressed rock sample; lifting the vacuum transparent shield through a counterweight structure; arranging the uniaxially compressed rock sample between two sample pads; filling an interior of a heat conduction cavity with high thermal conductivity powder, so that a space between the uniaxially compressed rock sample and a liquid nitrogen refrigeration circulating pipe or an electromagnetic heating plate is surrounded by the high thermal conductivity powder;

installing a transverse deformation sensor; and arranging a temperature sensor and an acoustic emission sensor inside the heat conduction cavity;

releasing the counterweight structure to make the vacuum transparent shield and the vacuum base form the vacuum structure; and moving a vacuum structure to a loading space through a mobile cart, and fixing the vacuum structure at a loading position;

applying a preload of 100 N to the uniaxially compressed rock sample through an oil cylinder, so that a pressure head presses down until a loading force comes into contact with the uniaxially compressed rock sample;

evacuating the vacuum structure through a vacuum pumping pipe using a vacuum pump to reach a target vacuum degree;

setting a target temperature and a temperature loading rate through a dual-channel PID controller; and arranging a light source, a high-speed camera and an infrared thermal imaging device outside the vacuum structure to monitor evolution of surface deformation field of the uniaxially compressed rock sample in real time; and carrying out mechanical loading on the uniaxially compressed rock sample through the loading cylinder, and synchronously conducting optical observation and acoustic emission monitoring to obtain load, displacement and deformation results during a uniaxial compression process; and conducting supplementary analysis on the evolution of the surface deformation field of the uniaxially compressed rock sample monitored in real time by using a digital image correlation method, and analyzing laws of acoustic emission signals during a fracture process of the uniaxially compressed rock sample at the same time.

Compared to traditional synthesis methods, it offers the following advantages.

The system for testing rock fracture under a vacuum and extreme-temperature condition provided in the present disclosure mainly includes three parts. The first part is the vacuum extreme-temperature loading structure, which mainly provides a vacuum environment for the sample and simulates an extreme high temperature or extreme low temperature environment. The second part is the overall loading frame structure, which mainly provides a loading force for the sample to simulate the breaking force on the rock when crushing the rock. The third part is the mobile cart, which is mainly used to move the vacuum extreme-temperature loading structure to a specified position in the loading space of the overall frame. The vacuum extreme-temperature loading structure includes a vacuum transparent shield and a vacuum base. A vacuum structure is formed by the vacuum transparent shield and the vacuum base to provide a vacuum environment for the sample. The vacuum extreme-temperature loading structure also includes an extreme-temperature loading module. The extreme temperature loading module mainly provides an extreme high temperature or extreme low temperature environment for the sample. The vacuum environment has a very weak thermal conductivity, which can reduce the diffusion of the extreme high temperature or extreme low temperature environment to the entire vacuum structure and prevent damage to other structures of the system. At the same time, the extreme-temperature loading module is also used to monitor deformation and fracture sound of the sample when it is subjected to the loading force in the extreme high temperature or extreme low temperature environment. The overall loading frame structure includes an overall frame and a loading cylinder. A middle of the overall frame is provided with a loading space, which is mainly used for placing the vacuum extreme-temperature loading structure while applying a loading force to the sample in the vacuum extreme-temperature loading structure through the loading cylinder. The mobile cart is located in the loading space and can slide inside and outside the loading space. The vacuum extreme-temperature loading structure is placed on the mobile cart, so that the vacuum extreme-temperature loading structure can be placed at a specified position within the loading space through the sliding of the mobile cart, which is convenient for the loading cylinder to apply the loading force. In summary, the system of the present disclosure integrates the extreme high temperature or extreme low temperature environment with the vacuum environment. At the same time, it couples the extreme high temperature and extreme low temperature environments in the same module, realizing the synchronous monitoring of rock loading and acoustics in a vacuum ultra-high temperature or ultra-low temperature environment.

BRIEF DESCRIPTION OF THE DRAWINGS

To more clearly illustrate the technical solutions in the embodiments of the present disclosure or in the prior art, the accompanying drawings used in the embodiments will be briefly introduced below. Obviously, the accompanying drawings in the following description are only some embodiments of the present disclosure. Other accompanying drawings can be obtained by one of ordinary skill in the art without paying creative labor.

Figure 1:
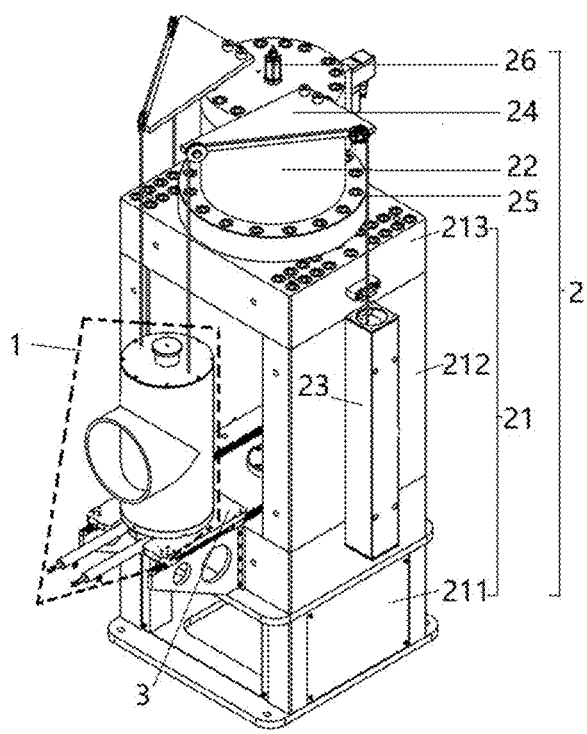
FIG. 1 is a schematic diagram of a system for testing rock fracture under a vacuum and extreme-temperature condition according to an embodiment of the present disclosure.

In the drawings:
1, vacuum extreme-temperature loading structure; 11, vacuum transparent shield; 12, vacuum base; 13, extreme-temperature loading module; 1301, vacuum support frame; 1302, loading bracket; 1303, longitudinal deformation sensor; 1304, loading pad; 1305, thermal isolation plate; 1306, loading block; 1307, pressure head; 1308, heat conduction cavity; 1309, sample pad; 1310, uniaxially compressed rock sample; 1311, vacuum liquid nitrogen delivery circulating pipe; 1312, liquid nitrogen refrigeration circulating pipe; 1313, electromagnetic heating plate; 1314, transverse deformation sensor; 14, vacuum pumping pipe; 15, observation port;
2, overall loading frame structure; 21, overall frame; 211, frame bottom column; 212, frame column; 213, frame crossbeam; 22, loading cylinder; 23, counterweight structure; 24, counterweight support frame; 25, counterweight rope; 26, displacement sensor;
3, mobile cart;
4, Brazilian splitting fixture; 41, liquid nitrogen circulation channel; 42, Brazilian splitting rock sample; 43, first temperature conduction back plate; 44, Brazilian splitting high-transparency material; and
5, variable-angle wedge shearing fixture; 51, wedge shearing rock sample; 52, second temperature conduction back plate; 53, wedge shearing highly-transparency material.

DETAILED DESCRIPTION OF EMBODIMENTS

Technical solutions in the embodiments of the present disclosure will be clearly and completely described with reference to the accompanying drawings in the present disclosure. Obviously, the described embodiments are only a part of the embodiments of the present disclosure. Based on these embodiments, all other embodiments obtained by those of ordinary skill in the art shall fall within the protection scope of the present disclosure.

Embodiment 1

Figure 2:
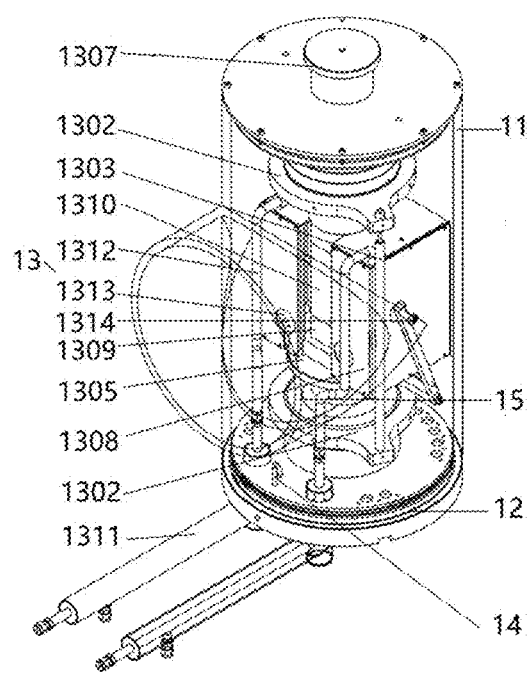
FIG. 2 is a three-dimensional (3D) schematic diagram of a vacuum extreme temperature loading structure of the system according to an embodiment of the present disclosure.
Figure 3:
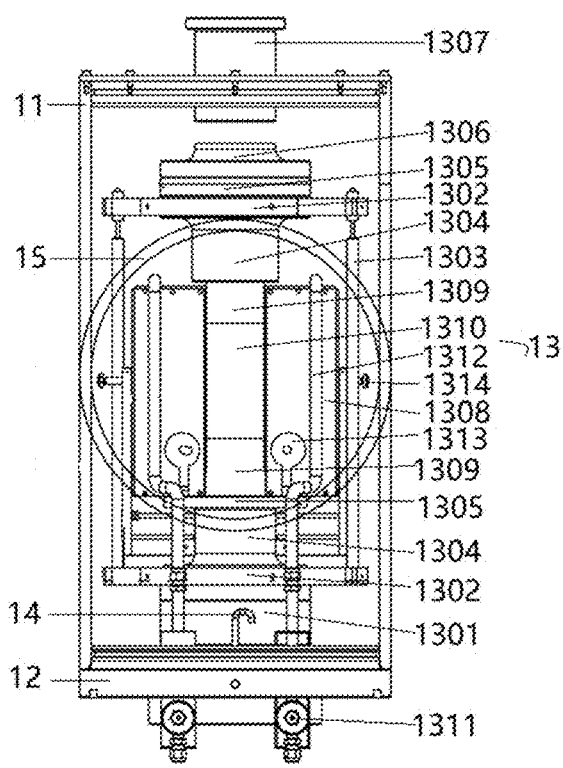
FIG. 3 is a cross-sectional view of the loading structure according to an embodiment of the present disclosure.
Figure 4:
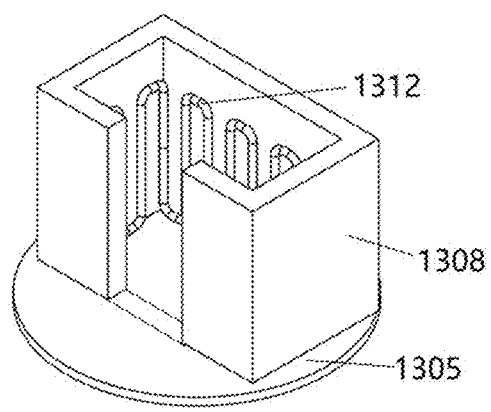
FIG. 4 is a schematic diagram of a liquid nitrogen refrigeration circulating tube in a heat conduction cavity of the system according to an embodiment of the present disclosure.
Figure 5:
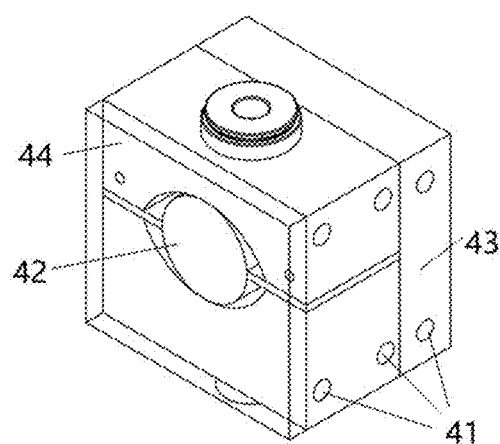
FIG. 5 is a schematic diagram of a Brazilian splitting fixture according to an embodiment of the present disclosure.
Figure 6:
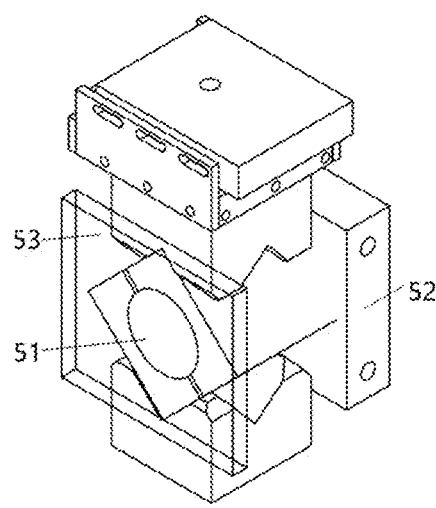
FIG. 6 is a schematic diagram of a variable-angle wedge shearing fixture according to an embodiment of the present disclosure.

As shown in FIGS. 1-6, a system for testing rock fracture under a vacuum and extreme-temperature condition is provided. The system includes a vacuum extreme-temperature loading structure 1, an overall loading frame structure 2 and a mobile cart 3. The vacuum extreme-temperature loading structure 1 includes a vacuum transparent shield 11, a vacuum base 12, and an extreme-temperature loading module 13. A bottom end of the vacuum transparent shield 11 is covered on the vacuum base 12 and is hermetically connected with the vacuum base 12 to form a vacuum structure. The extreme-temperature loading module 13 is provided in the vacuum structure. The overall loading frame structure 2 includes an overall frame 21 and a loading cylinder 22. A middle of the overall frame 21 is provided with a loading space, and the vacuum extreme-temperature loading structure 1 is located in the loading space. A center of a top end of the overall frame 21 is provided with a first loading through hole, and the loading cylinder 22 is located above the first loading through hole, so that a loading rod of the loading cylinder 22 passes through the first loading through hole to apply a loading force to the extreme temperature loading module 13. One end of the loading cylinder 22 is fixedly connected with the overall frame 21. The mobile cart 3 is located in the loading space and is slidably connected with the overall frame 21, and the vacuum base 12 is arranged on the mobile cart 3.

The system for testing rock fracture under a vacuum and extreme-temperature condition provided in the present disclosure mainly includes three parts. The first part is the vacuum extreme-temperature loading structure, which mainly provides a vacuum environment for the sample and simulates an extreme high temperature or extreme low temperature environment. The second part is the overall loading frame structure, which mainly provides a loading force for the sample to simulate the breaking force on the rock when crushing the rock. The third part is the mobile cart, which is mainly used to move the vacuum extreme-temperature loading structure to a specified position in the loading space of the overall frame. The vacuum extreme-temperature loading structure includes a vacuum transparent shield and a vacuum base. A vacuum structure is formed by the vacuum transparent shield and the vacuum base to provide a vacuum environment for the sample. The vacuum extreme-temperature loading structure also includes an extreme-temperature loading module. The extreme temperature loading module mainly provides an extreme high temperature or extreme low temperature environment for the sample. The vacuum environment has a very weak thermal conductivity, which can reduce the diffusion of the extreme high temperature or extreme low temperature environment to the entire vacuum structure and prevent damage to other structures of the system. At the same time, the extreme-temperature loading module is also used to monitor deformation and fracture sound of the sample when it is subjected to the loading force in the extreme high temperature or extreme low temperature environment. The overall loading frame structure includes an overall frame and a loading cylinder. A middle of the overall frame is provided with a loading space, which is mainly used for placing the vacuum extreme-temperature loading structure while applying a loading force to the sample in the vacuum extreme-temperature loading structure through the loading cylinder. The mobile cart is located in the loading space and can slide inside and outside the loading space. The vacuum extreme-temperature loading structure is placed on the mobile cart, so that the vacuum extreme-temperature loading structure can be placed at a specified position within the loading space through the sliding of the mobile cart, which is convenient for the loading cylinder to apply the loading force. In summary, the system of the present disclosure integrates the extreme high temperature or extreme low temperature environment with the vacuum environment. At the same time, it couples the extreme high temperature and extreme low temperature environments in the same module, realizing the synchronous monitoring of rock loading and acoustics in a vacuum ultra-high temperature or ultra-low temperature environment.

In some embodiments, the overall frame 21 includes a frame bottom column 211, a frame column 212 and a frame crossbeam 213. A sliding guide rail is provided on the frame bottom column 211, and pulleys of the mobile cart 3 are adapted to the sliding guide rail. The mobile cart 3 is slidably connected to the frame bottom column 211. The frame column 212 is provided with a loading space. The frame column 212 is located above the frame bottom column 211 and is fixedly connected to the frame bottom column 211. The frame crossbeam 213 is located above the frame column 212 and is fixedly connected to the frame column 212. A center of the frame crossbeam 213 is provided with a first loading through hole, and the loading cylinder 22 is located above the first loading through hole and is fixedly connected to the frame crossbeam 213.

Specifically, the bottom of the loading space is the frame bottom column. The loading space is used to place the vacuum extreme-temperature loading structure. A sliding guide rail is provided on the frame bottom column, and pulleys are installed on the mobile cart, enabling the mobile cart to move on the sliding guide rail that matches it through the pulleys.

In some embodiments, the overall loading frame structure 2 further includes two counterweight structures 23, two counterweight support frames 24, and two counterweight ropes 25. Each counterweight support frame is in a right-angled triangular structure. The two counterweight support frames 24 are symmetrically along an axis of the loading cylinder 22 and fixedly arranged at a first end of the loading cylinder 22. One leg of one of the two counterweight support frames 24 parallel to one leg of the other of the two counterweight support frames 24. Two ends of the hypotenuse of each counterweight support frame 24 are each fixedly provided with a support pulley. One end of each counterweight rope 25 is fixedly connected to a corresponding counterweight structure 23 through a first counterweight hook, and the other end of each counterweight rope 25 successively passes through the corresponding support pulley and is fixedly connected to the top of the vacuum transparent shield 11 through a second counterweight hook.

Specifically, the weight of the two counterweight structures is greater than the weight of the vacuum transparent shield. One end of the counterweight rope is connected to the counterweight structure, and the other end of the counterweight rope is connected to the vacuum transparent shield. Through the sliding of the counterweight rope on the support pulleys of the counterweight support frame, the vacuum transparent shield is lifted up by the action of gravity. When the vacuum transparent shield is required to be covered, it is only necessary to reduce the weight of the two counterweight structures, or remove the two counterweight structures, so that the vacuum transparent shield descends under the action of gravity and covers the vacuum base. After the sample is loaded, the vacuum transparent shield covers the vacuum base and is moved to the loading space by the mobile car. A positioning pin is arranged on the loading rod of the loading cylinder above the loading space to align the loading rod with the pressure head.

In some embodiments, the overall loading frame structure 2 further includes a displacement sensor 26, and the displacement sensor 26 is located at the center of a second end of the loading cylinder 22.

Specifically, the displacement sensor is arranged above the loading cylinder and at the center of the loading cylinder, which can monitor the situation of the loading force applied by the loading cylinder.

In some embodiments, the vacuum extreme-temperature loading structure 1 further includes a vacuum pumping pipe 14. An end of the vacuum pumping pipe 14 is located inside the vacuum transparent shield 11. The vacuum base 12 is provided with a vacuum pipe through hole. The other end of the vacuum pumping pipe 14 passes through the vacuum pipe through hole to be connected to a vacuum pump. An observation port 15 is provided on one side of the vacuum transparent shield 11, and the observation port 15 is sealed with a transparent anti-fog material.

Specifically, the vacuum structure formed by the vacuum transparent shield and the vacuum base is a closed environment. The vacuum pump is used to evacuate the vacuum structure through the vacuum pipe through hole, so that the vacuum structure is in a vacuum environment. A part of the vacuum pumping pipe is embedded in the vacuum base to achieve the evacuation of the vacuum structure, and the vacuum degree in the vacuum structure can reach 10 Pa. Since the simulation of an extreme high temperature or extreme low temperature environment will be carried out in the vacuum structure, during this process, due to the temperature difference between the inside and the outside of the vacuum structure, fog may appear on the wall of the vacuum transparent shield, which will blur the line of sight. Therefore, the observation port is provided and sealed with a transparent anti-fog material, which can avoid the problem of blurred vision caused by the temperature difference between the inside and the outside of the vacuum structure. In addition, the inside of the vacuum transparent shield can also be dried, and an anti-fog spray can be sprayed on the outer surface of the vacuum transparent shield to prevent frost formation on the outer surface of the vacuum transparent shield due to the temperature difference. Furthermore, a vacuum pressure valve is provided above the vacuum transparent shield, which can display the vacuum degree inside the vacuum structure.

In some embodiments, the extreme-temperature loading module 13 includes a vacuum support frame 1301, two loading brackets 1302, two longitudinal deformation sensors 1303, two loading pads 1304, two thermal isolation plates 1305, a loading block 1306 and a pressure head 1307. The vacuum support frame 1301 is located at the center of the vacuum base 12. The two loading brackets 1302 are each circular, and the central axes of the two loading brackets 1302 are the same as the central axis of the vacuum base 12. One of the loading brackets 1302 is located on the vacuum support frame 1301 and is fixedly connected to the vacuum support frame 1301. Each of the loading brackets 1302 has two symmetrical longitudinal support holes. One end of each of the longitudinal deformation sensors 1303 passes through a corresponding longitudinal support hole to be fixedly connected to one of the loading brackets 1302, and the other end of each of the longitudinal deformation sensors 1303 passes through a corresponding longitudinal support hole to be fixedly connected to the other loading bracket 1302. The two loading pads 1304 are each cylindrical, and the central axes of the two loading pads 1304 are the same as the central axis of the vacuum base 12. One of the two loading pads 1304 is located on and fixedly connected to one of the two loading brackets 1302, and the other of the two loading pads 1304 is located below and fixedly connected to the other of the two loading brackets 1302. The two thermal insulation plates 1305 are each circular, and the central axes of the two thermal insulation plates 1305 are the same as the central axis of the vacuum base 12. One of the two thermal insulation plates 1305 is located on and fixedly connected to one of the two loading pads 1304, and the other of the two thermal insulation plates 1305 is located above and fixedly connected to the other of the two loading brackets 1302. The loading block 1306 is located at the center of the other thermal insulation plate 1305 and is fixedly connected to the other thermal insulation plate 1305. The pressure head 1307 is cylindrical, and the position of the pressure head 1307 corresponds to that of the loading block 1306. A top end of the vacuum transparent shield 11 is provided with a second loading through hole, and one end of the pressure head 1307 passes through the second loading through hole and is hermetically and slidably connected to the vacuum transparent shield 11.

Specifically, the vacuum support frame is used to support the loading brackets. The two loading brackets serve as the main support of the extreme-temperature loading module. The two loading brackets are connected by two longitudinal deformation sensors in the middle. While the two longitudinal deformation sensors support the two loading brackets, they are also used to test the deformation of the sample in the longitudinal direction during the loading process. Since the two longitudinal deformation sensors are fixed in the external bracket and do not directly contact with the high-temperature and low-temperature regions, and the heat conduction efficiency in the vacuum environment is relatively low, the two longitudinal deformation sensors are less affected by temperature. In such cases, the measurement results are more accurate. The two loading pads are configured to support the heat conduction cavity and shorten the downward pressing distance of the pressure head under the condition of the applied loading force. The two thermal insulation plates are configured to isolate the temperature transmitted from the heat conduction cavity to avoid affecting other structures such as the loading cylinder. The loading block is configured to shorten the downward pressing distance of the pressure head under the condition of the applied loading force. The pressure head mainly moves downward by the loading force applied by the loading cylinder. The two longitudinal deformation sensors can be wirelessly connected to the external monitoring and display system. At the same time, the vacuum base can be also provided with through holes for the longitudinal deformation sensors, and the two longitudinal deformation sensors can be connected to the external monitoring and display system through the sensor cables.

In some embodiments, the extreme-temperature loading module 13 further includes a heat conduction cavity 1308, two sample pads 1309, a first vacuum liquid nitrogen delivery circulating pipe 1311, a second vacuum liquid nitrogen delivery circulating pipe 1311, a liquid nitrogen refrigeration circulating pipe 1312, and a plurality of electromagnetic heating plate 1313. The heat conduction cavity 1308 has a cubic hollow structure and is located on one of the thermal insulation plates 1305. The center of one side of the heat conduction cavity 1308 is provided with an observation channel adapted to a rock sample, and the position of the observation channel corresponds to that of the observation port 15. A top of the heat conduction cavity 1308 is provided with two through holes for the liquid nitrogen circulating pipes, and is also provided with a third loading through hole. The two sample pads 1309 are located inside the heat conduction cavity 1308, and the central axes of the two sample pads 1309 are the same as the central axis of the vacuum base 12. A uniaxially compressed rock sample 1310 is arranged between the two sample pads 1309. One of the sample pads 1309 is located at the bottom of the heat conduction cavity 1308, and the other sample pad 1309 passes through the third loading through hole to abut against the other loading pad 1304. A first end of the first vacuum liquid nitrogen delivery circulating pipe 1311 is connected to an outlet of the liquid nitrogen circulation tank, and a first end of the second vacuum liquid nitrogen delivery circulating pipe 1311 is connected to an inlet of the liquid nitrogen circulation tank. A first end of the liquid nitrogen refrigeration circulating pipe 1312 is connected to the second end of the first vacuum liquid nitrogen delivery circulating pipe 1311. The plurality of electromagnetic heating plates 1313 are arranged closely against the inner side wall of the heat conduction cavity 1308. The vacuum base 12 is also provided with two vacuum liquid nitrogen delivery holes and an electromagnetic heating guide hole. A second end of the liquid nitrogen refrigeration circulating pipe 1312 passes through one of the vacuum liquid nitrogen delivery holes and one of the liquid nitrogen circulating pipe through holes in sequence to enter the heat conduction cavity 1308. It is arranged at intervals with the plurality of the electromagnetic heating plates 1313 closely against the inner side wall of the heat conduction cavity 1308, and then passes through the other liquid nitrogen circulating pipe through hole and the other vacuum liquid nitrogen delivery hole in sequence to be connected to the second end of the second vacuum liquid nitrogen delivery circulating pipe 1311. The plurality of electromagnetic heating plates 1313 are connected in series through electromagnetic heating wires and pass through the electromagnetic heating guide hole to be connected to the power supply.

Specifically, the heat conduction cavity is mainly used for placing the test specimen and providing extremely high- or extremely low-temperature environments. One side of the heat conduction cavity is provided with an observation channel for observing the entire test specimen. This observation channel corresponds to the observation port, and the situation of the test specimen during the test process can be observed through the observation port and the observation channel. Two sample pads are located inside the heat conduction cavity, and the test specimen is positioned between the two sample pads. The heat conduction cavity is provided with a third loading through hole, and the sample pad located above the test specimen passes through the third loading through hole to contact with the loading pad when pressing down the pressure head. The two vacuum liquid nitrogen conveying circulating pipes are used for conveying liquid nitrogen into the liquid nitrogen refrigeration circulating pipe and outputting the liquid nitrogen in the liquid nitrogen refrigeration circulating pipe. The liquid nitrogen refrigeration circulating pipe is arranged in a circular manner and is closely attached to the inner side wall of the heat conduction cavity, and is used for providing an extremely low temperature environment. The plurality of electromagnetic heating plates are arranged at intervals from the liquid nitrogen refrigeration circulating pipe and closely attached to the inner side wall of the heat conduction cavity, which are used for providing an extremely high temperature environment. The low temperature environment and the high temperature environment are coupled together inside the heat conduction cavity, saving the equipment space. After the test specimen is installed in the heat conduction cavity, the heat conduction cavity needs to be filled with high thermal conductivity powder material, so that the space between the test specimen, the liquid nitrogen refrigeration circulating pipe and the electromagnetic heating plate is filled with the high thermal conductivity powder material to improve the heat conduction efficiency. The high thermal conductivity powder material can be graphene powder. The liquid nitrogen circulation tank is used for outputting and receiving liquid nitrogen.

In some embodiments, the extreme temperature loading module 13 further includes a transverse deformation sensor 1314, a temperature sensor and an acoustic emission sensor. Two ends of the transverse deformation sensor 1314 abut against and are fixed to the outer side wall of the heat conduction cavity 1308. The temperature sensor is arranged inside the heat conduction cavity 1308. The acoustic emission sensor is arranged inside the heat conduction cavity 1308.

Specifically, the transverse deformation sensor is used to test the deformation of the test specimen when it is subjected to the loading force. Since the transverse deformation sensor is fixed on the outer side of the heat conduction cavity and does not directly contact the high-temperature and low-temperature areas, and the heat conduction efficiency in the vacuum environment is relatively low, the transverse deformation sensor is less affected by the temperature, so the measurement result is more accurate. The temperature sensor is used to monitor the temperature of the environment where the test specimen is located. The acoustic emission sensor is used to monitor the sound when the test specimen cracks. The transverse deformation sensor, the temperature sensor and the acoustic emission sensor can be wirelessly connected to the external monitoring and display system. At the same time, the vacuum base can also be provided with the through hole for the transverse deformation sensor, the through hole for the temperature sensor and the through hole for the acoustic emission sensor, so that the transverse deformation sensor, the temperature sensor and the acoustic emission sensor are respectively connected to the external monitoring and display system through sensor cables.

In some embodiments, the extreme-temperature loading module 13 further includes a dual-channel PID controller and a vacuum liquid nitrogen delivery circulating pipe. The vacuum liquid nitrogen delivery circulating pipe includes a pressure sensor and an electric heater. Both the pressure sensor and the electric heater are arranged at the inlet of the vacuum liquid nitrogen conveying circulating pipe, and the pressure sensor and the electric heater are respectively connected to the first channel of the dual-channel PID controller. The electromagnetic heating plates 1313 are connected in series through an electromagnetic heating wire, and pass through the electromagnetic heating guide hole to be connected to the second channel of the dual-channel PID controller. The dual-channel PID controller is connected to the power supply.

Specifically, the dual-channel PID controller has two control channels, which can control the extremely high temperature and the extremely low temperature simultaneously. The liquid nitrogen needs a certain pressure to be delivered to the liquid nitrogen refrigeration circulating pipe, and the delivery rate of the liquid nitrogen is related to the pressure value. The input temperature of the liquid nitrogen is controlled by the electric heater. Under the condition of constant refrigeration capacity, different set temperatures are controlled by adjusting the power of the electric heater. The first channel of the dual-channel PID controller is used to control the feed speed and feed temperature of the liquid nitrogen, and the second channel of the dual-channel PID controller is used to control the heating temperature of the electromagnetic heating plate, so as to achieve independent control of the low temperature and the high temperature, and enable the low-temperature environment and the high-temperature environment to be used alternately.

Embodiment 2

As shown in FIGS. 1-6, this Embodiment provides a method for testing rock fracture under a vacuum and extreme-temperature condition using the system of Embodiment 1. The method includes the following steps. Speckles are prepared for a uniaxially compressed rock sample. The vacuum transparent shield is lifted through the counterweight structure. The uniaxially compressed rock sample is provided between two sample pads, and then an interior of the heat conduction cavity is filled with high thermal conductivity powder, so that a space between the uniaxially compressed rock sample and the liquid nitrogen refrigeration circulating pipe or the electromagnetic heating plate is surrounded by the high thermal conductivity powder. A transverse deformation sensor is installed, and a temperature sensor and an acoustic emission sensor are arranged inside the heat conduction cavity. A counterweight structure is released to make the vacuum transparent shield and the vacuum base form a vacuum structure. The vacuum structure is moved to a loading space through a mobile cart and is fixed at a loading position. A preload of 100 N is applied to the uniaxially compressed rock sample through an oil cylinder, so that the pressure head presses down until the loading force just comes into contact with the uniaxially compressed rock sample. After that, a vacuum pump is used to evacuate the inside of the vacuum structure through a vacuum pumping pipe to reach a target vacuum degree requirement. According to the test scheme, the target temperature and the temperature loading rate are set through the dual-channel PID controller. A light source, a high-speed camera and an infrared thermal imaging device are arranged outside the vacuum structure to monitor the evolution of the surface deformation field of the uniaxially compressed rock sample in real time. Mechanical loading is carried out on the uniaxially compressed rock sample through the loading cylinder, and optical observation and acoustic emission monitoring are synchronously conducted to obtain load, displacement and deformation results during the uniaxial compression process. Supplementary analysis is conducted on the evolution of the surface deformation field of the uniaxially compressed rock sample monitored in real time by using the digital image correlation method, and the laws of the acoustic emission signals during the fracture process of the uniaxially compressed rock sample are analyzed at the same time.

Specifically, the uniaxially compressed rock sample is placed in the system for testing the rock fracture under a vacuum and extreme-temperature condition, and the heat conduction cavity is filled with thermal conductivity powder, which can be graphene powder. After loading the sample, a temperature sensor and an acoustic emission sensor are arranged inside the heat conduction cavity. The temperature where the sample is located and the sound situation when the sample fractures are monitored through the temperature sensor and the acoustic emission sensor, respectively. Then, the vacuum transparent shield covers the vacuum base to form a vacuum structure, which is moved to a designated loading position in the loading space by a mobile car. A preloading force is applied to make the pressure head contact the loading block and the loading pad contact the sample pad. After that, the interior of the vacuum structure is evacuated to create a vacuum environment, and the vacuum degree inside the vacuum structure can reach 10 Pa. The target temperature and the temperature loading rate are set through the dual-channel PID controller. If it is an extremely low-temperature environment, the temperature and the feed rate of the liquid nitrogen are controlled through the first channel of the dual-channel PID controller, and the lowest temperature can reach −180° C. If it is an extremely high-temperature environment, the temperature of the electromagnetic heating plate is controlled through the second channel of the dual-channel PID controller, and the highest temperature can reach 400° C. Then, a light source, a high-speed camera, and an infrared thermal imaging device are arranged outside the vacuum structure. When the sample is in the designed vacuum temperature environment, loading is carried out through the loading cylinder, and pressure is applied to the sample when the pressure head is pressing down. The deformation of the sample is monitored by the longitudinal deformation sensor and the transverse deformation sensor. The evolution of the surface deformation field of the uniaxially compressed rock sample is monitored in real time by the high-speed camera and the infrared thermal imaging device. Combined with the sound situation of the sample fracture monitored by the acoustic emission sensor, the analysis of rock fracture under vacuum and extreme-temperature conditions is carried out. Furthermore, the uniaxial compression fixture of the system for testing the rock fracture under vacuum and extreme-temperature conditions used herein can be placed with a Brazilian splitting fixture and a variable-angle wedge shear fixture, so as to realize different rock mechanical tests. When carrying out the Brazilian splitting test, the Brazilian splitting fixture is provided with a liquid nitrogen circulation channel 41 for the liquid nitrogen refrigeration circulating pipe to pass through, and a first temperature conduction back plate 43 is added behind the Brazilian splitting rock sample 42 of the Brazilian splitting fixture, so as to realize the temperature conduction of the Brazilian splitting rock sample 42 from different directions and improve the temperature conduction efficiency. A Brazilian splitting high-transparency material 44 is arranged in front of the Brazilian splitting rock sample 42 to increase the contact between the Brazilian splitting rock sample 42 and the first temperature conduction back plate 43 without blocking the observation of the fracture of the Brazilian splitting rock sample 42. When carrying out the variable-angle wedge shearing test, a second temperature conduction back plate 52 is added behind a wedge shearing rock sample 51 of the variable-angle wedge shearing fixture to realize the temperature conduction of the wedge shearing rock sample 51 from different directions and improve the temperature conduction efficiency. A wedge shear high-transparency material 53 is arranged in front of the wedge shearing rock sample 51 to increase the contact between the wedge shearing rock sample 51 and the second temperature conduction back plate 52 without blocking the observation of the fracture of the wedge shearing rock sample 51.

It should be noted that the method for testing rock fractures under vacuum and extreme-temperature conditions in Embodiment 2 is used for the operation of the system provided in Embodiment 1. Therefore, the performance principle of the system will not be elaborated here. The parts not described in detail can refer to Embodiment 1.

The preferred specific embodiments of the present disclosure are described above in detail. It should be understood that many modifications and changes can be made by one of ordinary skill in the art according to the concept of the present disclosure without creative efforts. Therefore, all technical solutions that can be obtained by one of ordinary skill in the art based on the existing technology through logical analysis, reasoning, or limited experiments according to the concept of the present disclosure shall fall within the protection scope defined by the claims.

What is claimed is:

1. A system for testing rock fracture under a vacuum and extreme-temperature condition, comprising:
    a vacuum extreme-temperature loading structure;
    an overall loading frame structure; and
    a mobile cart;
    wherein the vacuum extreme-temperature loading structure comprises a vacuum transparent shield, a vacuum base, and an extreme-temperature loading module; a bottom end of the vacuum transparent shield is covered on the vacuum base and is hermetically connected with the vacuum base to form a vacuum structure; and the extreme-temperature loading module is provided inside the vacuum structure;
    the overall loading frame structure comprises an overall frame and a loading cylinder; a middle of the overall frame is provided with a loading space, and the vacuum extreme-temperature loading structure is located in the loading space; a center of a top end of the overall frame is provided with a first loading through hole, and the loading cylinder is located above the first loading through hole to enable a loading rod of the loading cylinder to pass through the first loading through hole to apply a loading force to the extreme-temperature loading module; an end of the loading cylinder is fixedly connected with the overall frame; the loading cylinder is configured to apply the loading force to a uniaxially compressed rock sample in the vacuum extreme-temperature loading structure; and
    the mobile cart is located in the loading space and is slidably connected with the overall frame, and the vacuum base is arranged on the mobile cart;
    the extreme-temperature loading module further comprises:
    a heat conduction cavity;
    a first vacuum liquid nitrogen delivery circulating pipe;
    a second vacuum liquid nitrogen delivery circulating pipe;
    a liquid nitrogen refrigeration circulating pipe;
    a plurality of electromagnetic heating plate;
    a transverse deformation sensor,
    an acoustic emission sensor; and
    a temperature sensor;
    wherein the heat conduction cavity has a cubic hollow structure; a top of the heat conduction cavity is provided with two liquid nitrogen circulating pipe through holes;
    a first end of the first vacuum liquid nitrogen delivery circulating pipe is connected to an outlet of a liquid nitrogen circulation tank, and a first end of the second vacuum liquid nitrogen delivery circulating pipe is connected to an inlet of the liquid nitrogen circulation tank;

a first end of the liquid nitrogen refrigeration circulating pipe is connected to a second end of the first vacuum liquid nitrogen delivery circulating pipe;

the plurality of electromagnetic heating plates are arranged in the heat conduction cavity and closely against an inner side wall of the heat conduction cavity;

two ends of the transverse deformation sensor are configured to abut against and be fixed to an outer side wall of the heat conduction cavity;

the acoustic emission sensor is arranged inside the heat conduction cavity;

the temperature sensor is arranged inside the heat conduction cavity; and the vacuum base is also provided with two vacuum liquid nitrogen delivery holes and an electromagnetic heating guide hole; a second end of the liquid nitrogen refrigeration circulating pipe is configured to passes through one of the two vacuum liquid nitrogen delivery holes and one of the two liquid nitrogen circulating pipe through holes in sequence to enter the heat conduction cavity; the second end of the liquid nitrogen refrigeration circulating pipe is arranged at intervals with the plurality of the electromagnetic heating plates closely against the inner side wall of the heat conduction cavity, and then passes through the other of the two liquid nitrogen circulating pipe through holes and the other of the two vacuum liquid nitrogen delivery holes in sequence to be connected to the second end of the second vacuum liquid nitrogen delivery circulating pipe; and the plurality of electromagnetic heating plates are connected in series through electromagnetic heating wires and pass through the electromagnetic heating guide hole to be connected to a power supply;

the overall loading frame structure further comprises a displacement sensor, and the displacement sensor is located at a center of a second end of the loading cylinder.

2. The system of claim 1, wherein the overall frame comprises a frame bottom column, a frame column and a frame crossbeam;

a sliding guide rail is provided on the frame bottom column, and pulleys of the mobile cart are adapted to the sliding guide rail; and the mobile cart is slidably connected to the frame bottom column;

the frame column is provided with a loading space; and the frame column is located above the frame bottom column and is fixedly connected to the frame bottom column;

the frame crossbeam is located above the frame column and is fixedly connected to the frame column; and a center of the frame crossbeam is provided with a first loading through hole; and the loading cylinder is located above the first loading through hole and is fixedly connected to the frame crossbeam.

3. The system of claim 2, wherein the overall loading frame structure further comprises two counterweight structures, two counterweight support frames and two counterweight ropes;

each of the two counterweight support frames is in a right-angled triangular structure; the two counterweight support frames are symmetrically along an axis of the loading cylinder and are fixedly arranged at a first end of the loading cylinder; two ends of a hypotenuse of each of the two counterweight support frames are each fixedly provided with a support pulley; and one end of each of the two counterweight ropes is fixedly connected to a counterweight structure corresponding thereto through a first counterweight hook, and the other end of each of the two counterweight ropes successively passes through the support pulley corresponding thereto and is fixedly connected to the top of the vacuum transparent shield through a second counterweight hook.

4. The system of claim 3, wherein the vacuum extreme-temperature loading structure further comprises a vacuum pumping pipe; and a first end of the vacuum pumping pipe is located inside the vacuum transparent shield;

the vacuum base is provided with a vacuum pipe through hole; a second end of the vacuum pumping pipe passes through the vacuum pipe through hole to be connected to a vacuum pump; and an observation port is provided on one side of the vacuum transparent shield, and is sealed with a transparent anti-fog material.

5. The system of claim 4, wherein the extreme-temperature loading module comprises:

a vacuum support frame;
a first loading bracket;
a second loading bracket;
two longitudinal deformation sensors;
a first loading pad;
a second loading pad;
a first thermal isolation plate;
a second thermal isolation plate;
a loading block; and
a pressure head;

wherein the vacuum support frame is located at the center of the vacuum base;

the first loading bracket and the second loading bracket are each circular, and central axes of the first loading bracket and the second loading bracket are the same as a central axis of the vacuum base; the second loading bracket is located on and fixedly connected to the vacuum support frame; and each of the first loading bracket and the second loading bracket is provided with two symmetrical longitudinal support holes;

one end of each of the two longitudinal deformation sensors is configured to pass through a longitudinal support hole corresponding thereto to be fixedly connected to the first loading bracket, and the other end of each of the two longitudinal deformation sensors is configured to pass through a longitudinal support hole corresponding thereto to be fixedly connected to the second loading bracket;

the first loading pad and the second loading pad are each cylindrical, and central axes of the first loading pad and the second loading pad are the same as the central axis of the vacuum base; the second loading pad is located above and fixedly connected to the second loading bracket, and the first loading pad is located below and fixedly connected to the first loading bracket;

the first thermal insulation plate and the second thermal insulation plate are each circular, and central axes of the first thermal insulation plate and the second thermal insulation plate are the same as the central axis of the vacuum base; the first thermal insulation plate is located above and fixedly connected to the first loading pad, and the second thermal insulation plate is located above and fixedly connected to the second loading bracket;

the loading block is located at a center of the first thermal insulation plate and is fixedly connected to the first thermal insulation plate;

the pressure head is cylindrical, and a position of the pressure head corresponds to that of the loading block; and a top end of the vacuum transparent shield is provided with a second loading through hole; and one end of the pressure head passes through the second loading through hole and is hermetically and slidably connected to the vacuum transparent shield.

6. The system of claim 5, wherein the heat conduction cavity is located on the second thermal insulation plate; a center of one side of the heat conduction cavity is provided with an observation channel adapted to a rock sample, and a position of the observation channel corresponds to that of the observation port; the top of the heat conduction cavity is also provided with a third loading through hole;

the extreme-temperature loading module further comprises:

two sample pads;

the two sample pads are located inside the heat conduction cavity, and central axes of the two sample pads are the same as the central axis of the vacuum base; the uniaxially compressed rock sample is arranged between the two sample pads; one of the two sample pads is located at a bottom of the heat conduction cavity, and the other of the two sample pads is configured to pass through the third loading through hole to abut against the first loading pad.

7. The system of claim 6, wherein the extreme-temperature loading module further comprises a dual-channel proportion integration differentiation (PID) controller and a liquid nitrogen temperature control loop;

the liquid nitrogen temperature control loop comprises a pressure sensor and an electric heater; both the pressure sensor and the electric heater are arranged at an inlet of each of the first vacuum liquid nitrogen delivery circulating pipe and the second vacuum liquid nitrogen delivery circulating pipe, and the pressure sensor and the electric heater are respectively connected to a first channel of the dual-channel PID controller; and the plurality of electromagnetic heating plates are connected in series through the electromagnetic heating wires, and pass through the electromagnetic heating guide hole to be connected to a second channel of the dual-channel PID controller; and the dual-channel PID controller is connected to the power supply.

8. A method for testing rock fracture under a vacuum and extreme-temperature condition using the system of claim 7, comprising:

preparing speckles for a uniaxially compressed rock sample; lifting the vacuum transparent shield through a counterweight structure; arranging the uniaxially compressed rock sample between two sample pads; filling an interior of a heat conduction cavity with high thermal conductivity powder, so that a space between the uniaxially compressed rock sample and a liquid nitrogen refrigeration circulating pipe or an electromagnetic heating plate is surrounded by the high thermal conductivity powder;

installing a transverse deformation sensor; and arranging a temperature sensor and an acoustic emission sensor inside the heat conduction cavity;

releasing the counterweight structure to make the vacuum transparent shield and the vacuum base form the vacuum structure; and moving the vacuum structure to a loading space through a mobile cart, and fixing the vacuum structure at a loading position;

applying a preload of 100 N to the uniaxially compressed rock sample through an oil cylinder, so that a pressure head presses down until a loading force comes into contact with the uniaxially compressed rock sample; evacuating the vacuum structure through a vacuum pumping pipe using a vacuum pump to reach a target vacuum degree;

setting a target temperature and a temperature loading rate through a dual-channel PID controller; and arranging a light source, a high-speed camera and an infrared thermal imaging device outside the vacuum structure to monitor evolution of surface deformation field of the uniaxially compressed rock sample in real time; and carrying out mechanical loading on the uniaxially compressed rock sample through the loading cylinder, and synchronously conducting optical observation and acoustic emission monitoring to obtain load, displacement and deformation results during a uniaxial compression process; and conducting supplementary analysis on the evolution of the surface deformation field of the uniaxially compressed rock sample monitored in real time by using a digital image correlation method, and analyzing laws of acoustic emission signals during a fracture process of the uniaxially compressed rock sample at the same time.

\* \* \* \* \*